United States Patent
Wervey

(10) Patent No.: US 11,129,265 B2
(45) Date of Patent: Sep. 21, 2021

(54) METHODS AND SYSTEMS FOR COMPOSITE RADIATION SHIELDING PARTS

(71) Applicant: GE Precision Healthcare LLC, Milwaukee, WI (US)

(72) Inventor: Paul Michael Wervey, Mukwonago, WI (US)

(73) Assignee: GE PRECISION HEALTHCARE LLC, Milwaukee, WI (US)

(*) Notice: Subject to any disclaimer, the term of this patent is extended or adjusted under 35 U.S.C. 154(b) by 5 days.

(21) Appl. No.: 16/705,001

(22) Filed: Dec. 5, 2019

(65) Prior Publication Data
US 2021/0176851 A1 Jun. 10, 2021

(51) Int. Cl.
| | | |
|---|---|---|
| H05G 1/54 | (2006.01) | |
| H01J 35/16 | (2006.01) | |
| G21F 3/00 | (2006.01) | |
| G21F 1/12 | (2006.01) | |
| A61B 6/10 | (2006.01) | |

(52) U.S. Cl.
CPC ............. *H05G 1/54* (2013.01); *A61B 6/107* (2013.01); *G21F 1/12* (2013.01); *G21F 3/00* (2013.01); *H01J 35/16* (2013.01); *H01J 2235/165* (2013.01)

(58) Field of Classification Search
CPC .. H05G 1/54; A61B 6/107; G12F 1/12; G21F 3/00; H01J 35/16
See application file for complete search history.

(56) References Cited

U.S. PATENT DOCUMENTS

| | | | | |
|---|---|---|---|---|
| 3,774,037 | A * | 11/1973 | Backus | G21F 5/005 250/506.1 |
| 2003/0168637 | A1 | 9/2003 | McCord | |
| 2005/0084072 | A1* | 4/2005 | Pinchot | G21K 1/025 378/154 |
| 2013/0177131 | A1* | 7/2013 | Teng | A61B 6/06 378/4 |
| 2017/0294244 | A1* | 10/2017 | Benson | G21F 5/04 |
| 2019/0111480 | A1* | 4/2019 | Barbati | B33Y 80/00 |

\* cited by examiner

*Primary Examiner* — Hugh Maupin
(74) *Attorney, Agent, or Firm* — McCoy Russell LLP

(57) ABSTRACT

Various methods and systems are provided for a radiation shielding component including a plurality of parts fused together by metal infiltrated through junctions between adjacent, interconnected parts. In one embodiment, members on a side of a panel may be interlocked with indentations on a side of another and then metal may be infiltrated through a junction between the two panels to fuse the adjacent panels.

20 Claims, 6 Drawing Sheets

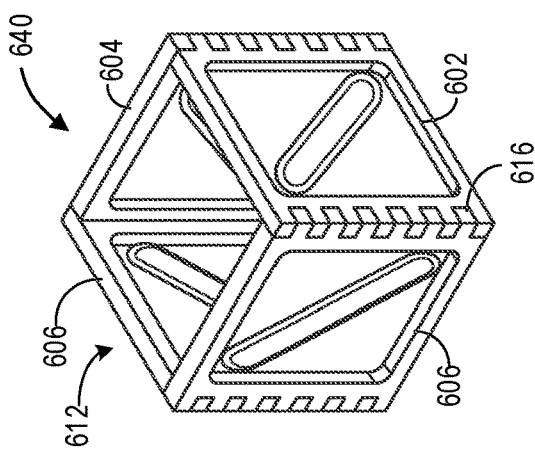
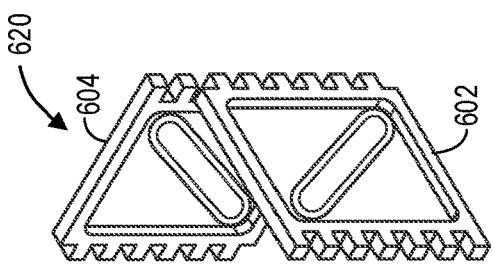
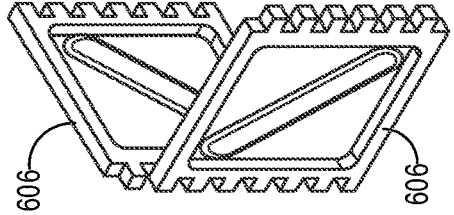
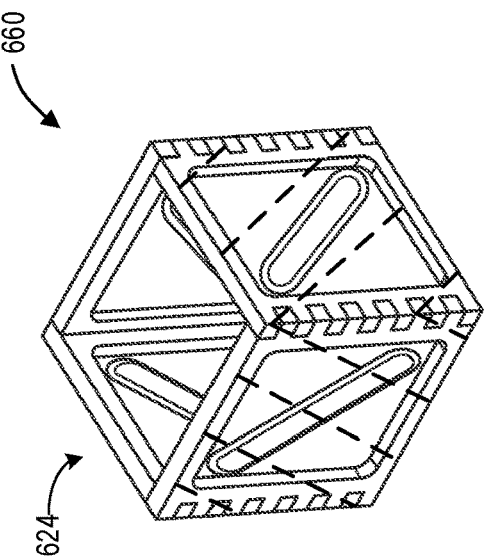
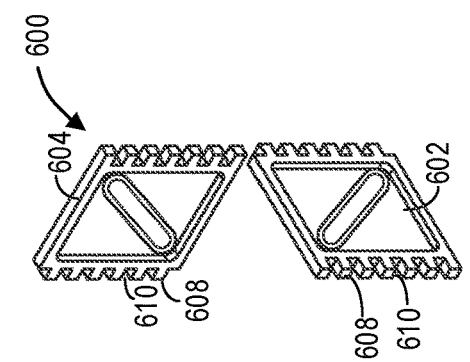
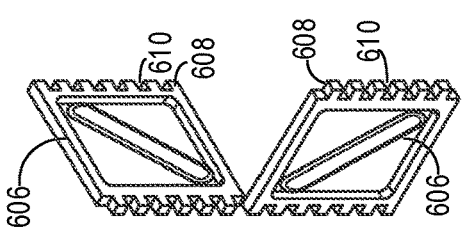
FIG. 6A  FIG. 6B  FIG. 6C  FIG. 6D  FIG. 6E

METHODS AND SYSTEMS FOR COMPOSITE RADIATION SHIELDING PARTS

FIELD

Embodiments of the subject matter disclosed herein relate to a radiation shielding component of an imaging apparatus including complementary interlocking members fused by copper infiltration.

BACKGROUND

Noninvasive imaging modalities may transmit energy in the form of x-ray radiation into an imaging subject. Based on the transmitted energy, images may be subsequently generated indicative of the structural or functional information internal to the imaging subject. In a computed tomography (CT) imaging system, an x-ray source generates a beam of x-ray radiation that is transmitted from the x-ray source through a collimator and the imaging subject to an x-ray detector.

An x-ray source typically comprises an x-ray tube including a cathode and an anode electrically connected to a high voltage electrical circuit. Upon the energization of the electrical circuit, which produces a potential difference of, for example, 60 kV to 140 kV, electrons are directed from the cathode to the anode. The electrons strike the anode (target) and produce high frequency electromagnetic waves, such as x-rays, and residual thermal energy. The residual energy is absorbed by the components within x-ray tube as heat. Since the x-rays are generated in all directions, the cathode and the anode may be enclosed in a radiation shield in order absorb scattered X-ray radiation and to direct the x-rays in a specific direction, such as towards the imaging subject.

Upon generation of the x-ray beam in the x-ray tube, the x-ray beam is collimated by passing the x-ray beam through a collimator having at least two collimatorblades. Once collimated to a desired x-ray beam size, the x-ray beam exits the collimator through a specific port. A part of the x-ray beam may be reflected from the collimator blades and is absorbed by a radiation shield enclosing the collimator. The radiation shield enclosing the x-ray tube and the collimator may be made of heavy metals such as tungsten or another heavy metal. A reliable process is employed to manufacture such radiation shields using heavy metals which typically has a high melting point and is hard. Also, the radiation shield may include components of different geometries.

BRIEF DESCRIPTION

In one embodiment, a system comprises a radiation shielding component including a plurality of interconnected parts with metal infiltrated across junctions between members of adjacent parts.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below:

FIG. 6A shows four panels of the radiation shielding component.

FIG. 6B shows the four panels of the radiation shielding component with the complementary interlocking members of each panel proximal to that of a respective adjacent panel.

FIG. 6C shows the four panels arranged in the form of the radiation shielding component with complementary geometries of adjacent panels in face sharing contact.

FIG. 6D shows the arranged panels of radiation shielding component including a metal.

FIG. 6E shows the radiation shielding component with adjacent panels fused by infiltrating with a metal.

DETAILED DESCRIPTION

Figure 1:
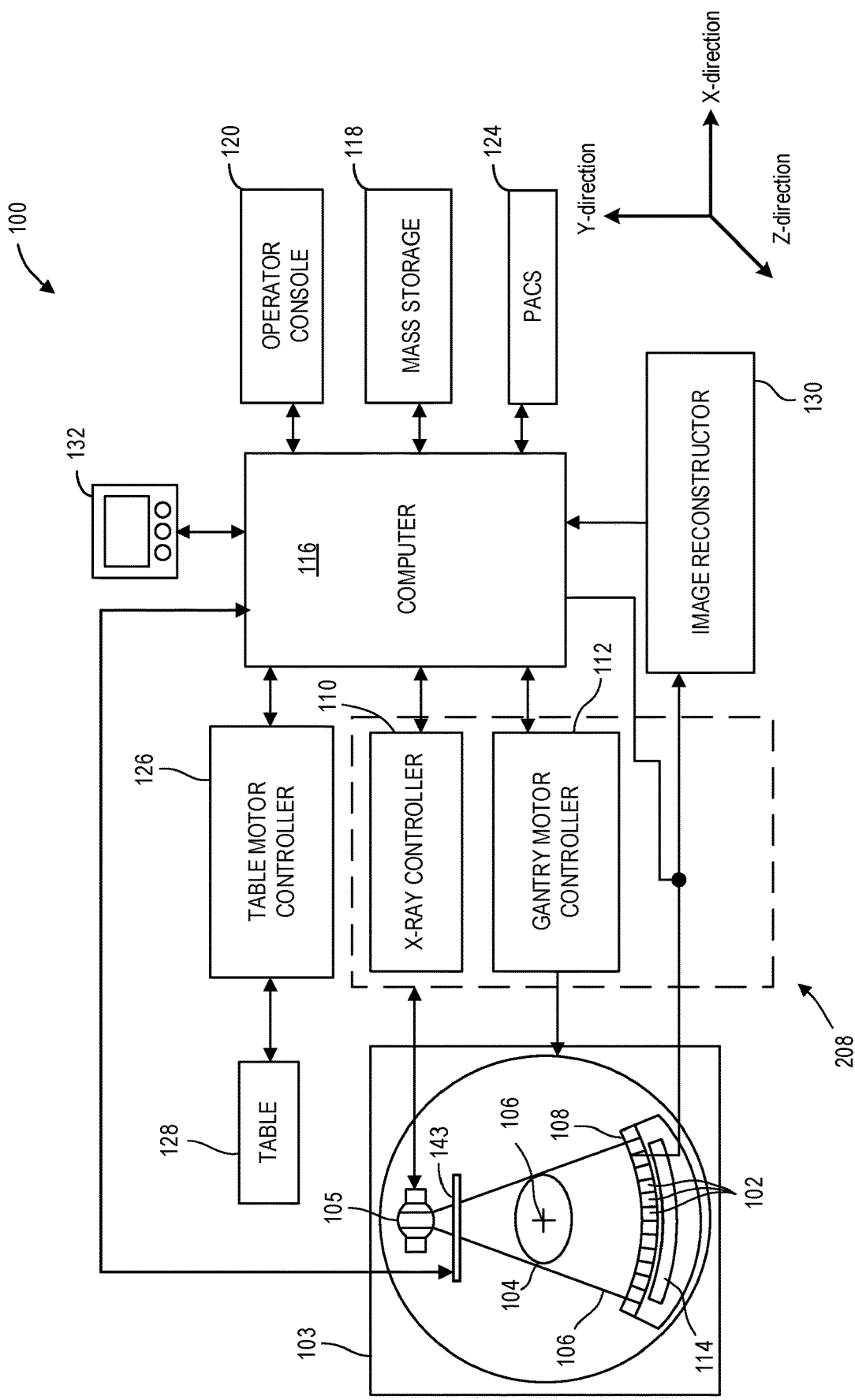
FIG. 1 shows a block schematic diagram of an exemplary imaging system according to an embodiment.
Figure 2:
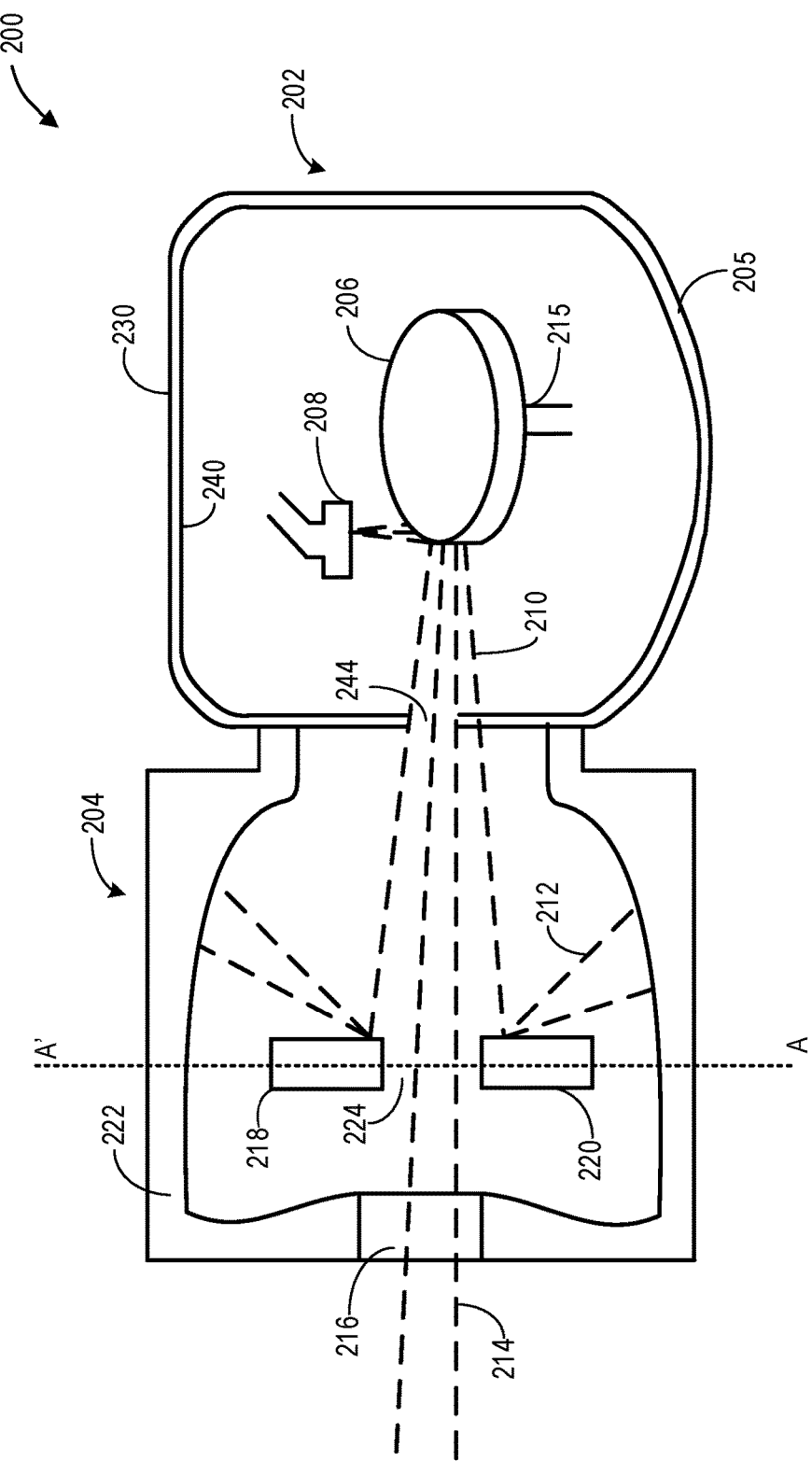
FIG. 2 shows a schematic diagram of an x-ray source used in the imaging system.
Figure 3:
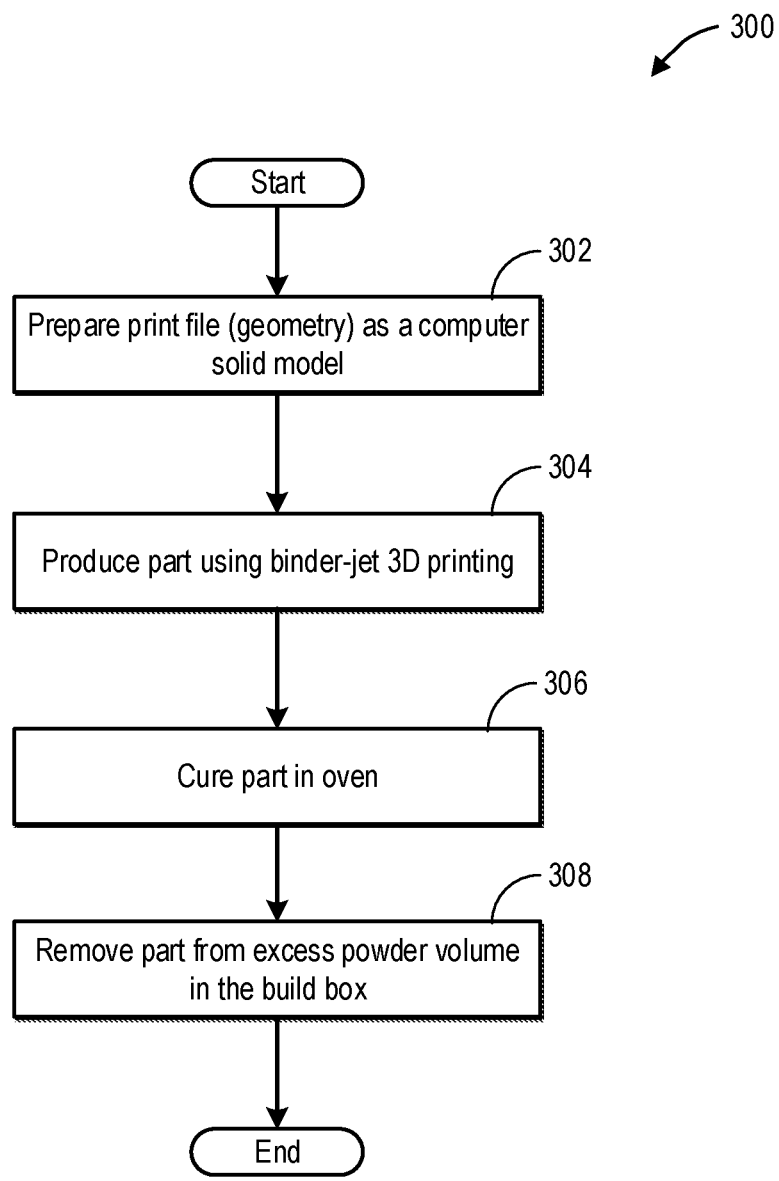
FIG. 3 shows a flow chart of an example method for manufacturing a radiation shielding component via binder-jet printing.
Figure 4:
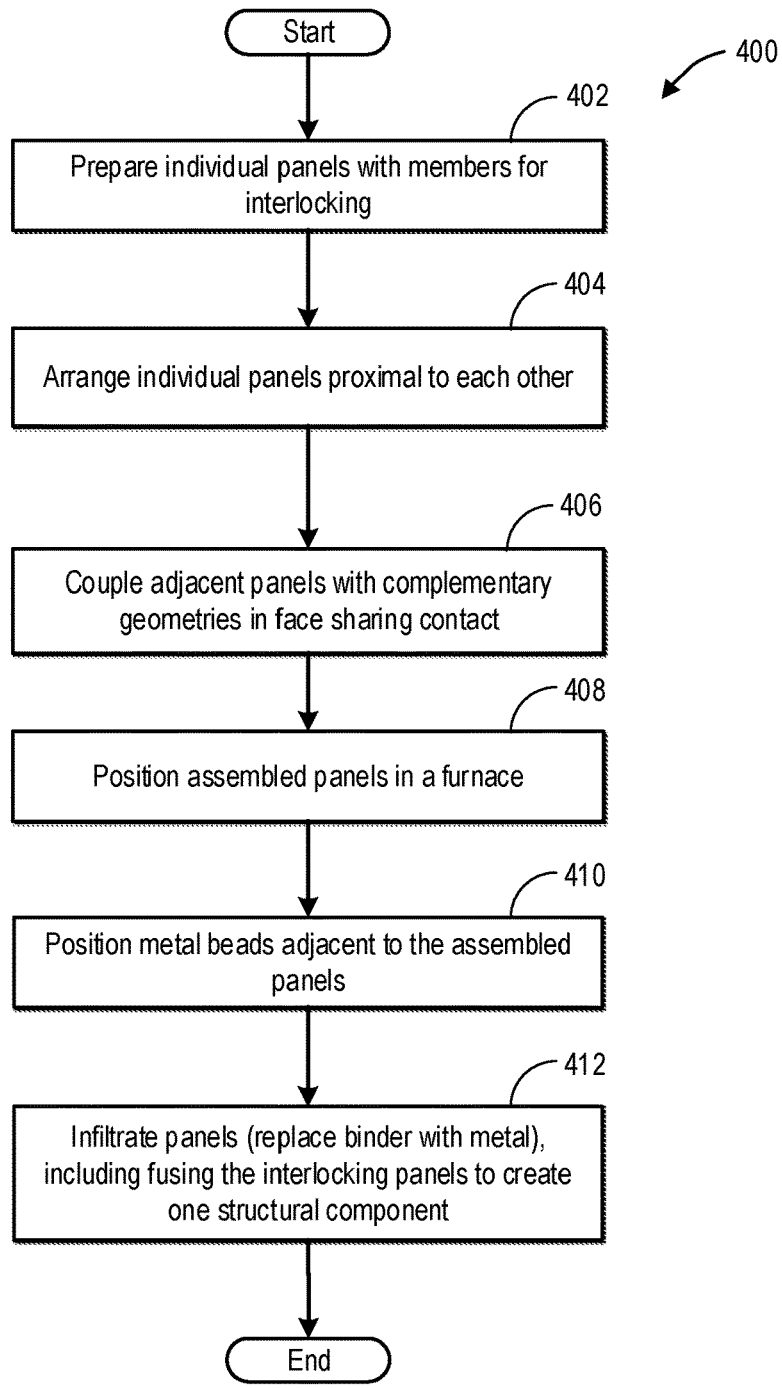
FIG. 4 shows a flow chart of an example method for manufacturing the interconnected radiation shielding component by infiltrating metal between adjacent panels.
Figure 5:
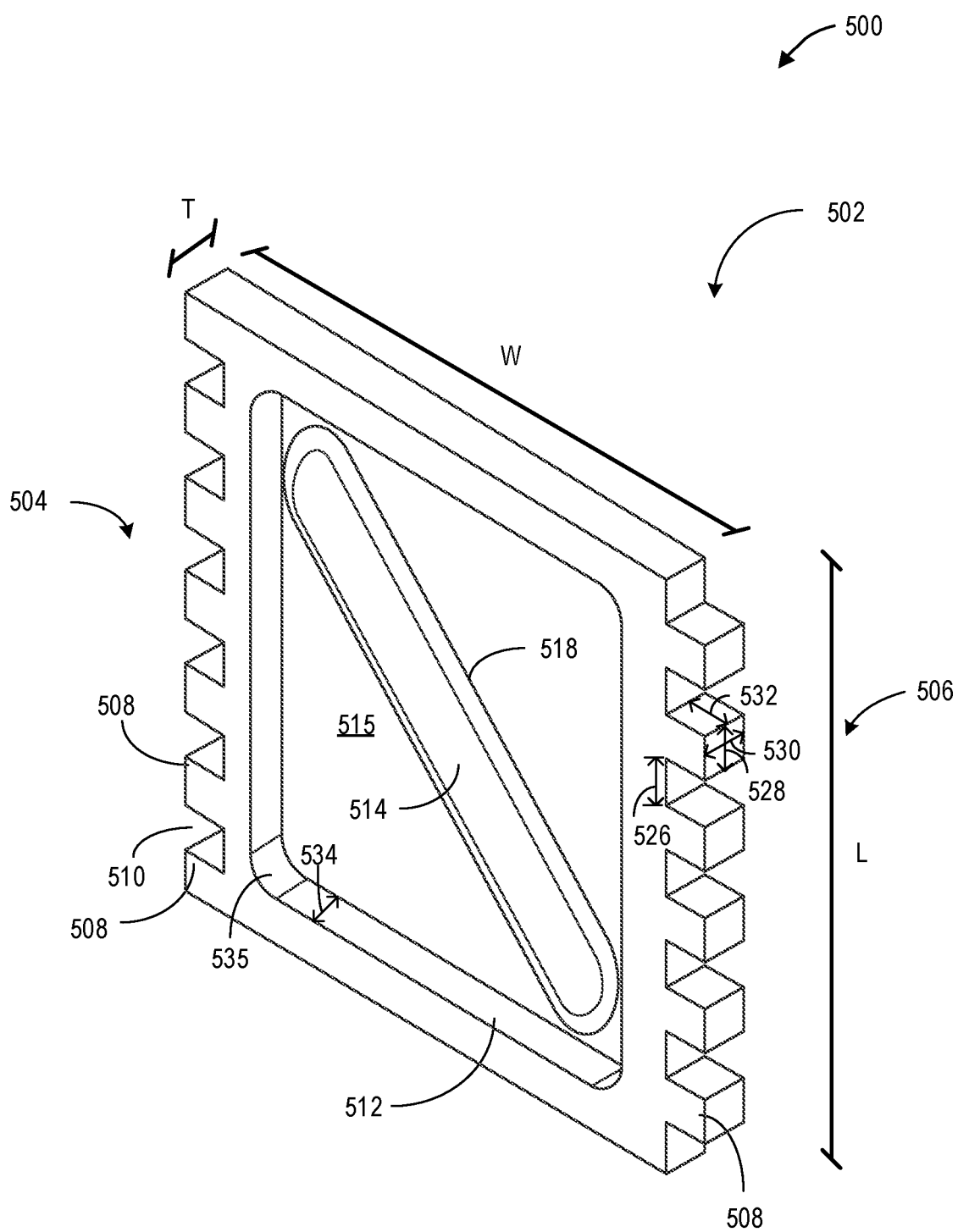
FIG. 5 shows a single panel of the radiation shielding component with complementary interlocking members.

The following description relates to various embodiments of radiation shielding manufacturing for an imaging apparatus. In particular, systems and methods are provided for methods for manufacturing a radiation shielding component of an imaging apparatus. FIG. 1 shows an example embodiment of an imaging system, wherein radiation shielding is included within an x-ray source. An x-ray source including an x-ray tube and a collimator at least partly enclosed within a radiation shielding is shown in FIG. 2. The radiation shielding component of the x-ray source may be made of tungsten or other heavy metal. FIG. 3 shows an example method for manufacturing the radiation shielding included in the x-ray source via a binder-jet 3D printing process. A single panel of the radiation shielding component with a high aspect ratio is shown in FIG. 5. The radiation shield may include an interconnected radiation shielding component comprising a plurality of individual panels with complementary geometries. FIG. 4 shows an example method for manufacturing the radiation shielding component by infiltrating metal between adjacent panels. A series of steps used in the manufacturing process of the radiation shielding component is shown in FIGS. 6A-6E.

Though a CT system is described by way of example, it should be understood that the present techniques may also be useful for manufacturing components in imaging modalities, such as tomosynthesis, C-arm angiography, and so forth. The present discussion of a CT apparatus is provided merely as an example of one suitable imaging technique using radiation shields manufactured via mentioned casting methods.

Heavy metals such as tungsten is used for manufacturing a radiation shield included in an x-ray tube and collimator of an x-ray source used in a CT system. Attributed to its higher density, non-toxic, pollution-free property of tungsten, tungsten alloy and composites have become a popular material used in the shielding applications for x-ray and gamma radiation shielding.

However, due to hardness and high melting point, it is difficult and cost ineffective to manufacture tungsten parts through traditional machining and molding. Machining may require harder and wear resistant tools for machining tungsten. Molding requires the mold to survive the melting temperature of tungsten, 3422° C. Very few materials are capable of withstanding such high temperature.

One example approach to manufacture tungsten parts include using Electrical Discharge Machining (EDM) tungsten metal directly or mixing tungsten or tungsten precursors with thermal plastics and then injection molding the part. However, screws or adhesive are required for assembling such parts in the x-ray. Also, inclusion of non-heavy metal screws in shielding parts may compromise on the shielding properties of the part. Further, traditional machining add complexity to the parts and may incur functional defects due to multistep machining assembling. Also, machining tungsten can be limiting in terms of design flexibility. As an example, the radiation shield may not be desired to be of uniform thickness, however, machining of the tungsten sheet may not provide the flexibility to vary thickness in parts, thereby leading to manufacturing of thicker, heavier parts than desired.

FIG. 1 illustrates an exemplary imaging system 100 such as a CT system. In accordance with aspects of the present disclosure, the system 100 is configured to perform automatic exposure control responsive to user input. In one embodiment, the system 100 includes the detector array 108 (see FIG. 1). The detector array 108 further includes a plurality of detector elements 102 that together sense the x-ray beam 106 that pass through a subject 104 such as a patient to acquire corresponding projection data. Accordingly, in one embodiment, the detector array 108 is fabricated in a multi-slice configuration including the plurality of rows of cells or detector elements 102. In such a configuration, one or more additional rows of the detector elements 102 are arranged in a parallel configuration for acquiring the projection data.

The x-ray beam may be generated at x-ray source 105 including an x-ray tube. The x-ray tube may include a cathode and an anode electrically connected to a high voltage electrical circuit. Upon the energization of the electrical circuit, electrons directed from the cathode strike the anode (target) and produce high frequency electromagnetic waves, such as x-rays. Since the x-rays are generated in all directions, the x-ray tube may be enclosed in a radiation shield in order to direct the x-rays in a specific direction, such as towards a collimator. At the collimator, the beam is collimated to a desired beam size. A part of the beam may be reflected from the collimator blades may be adsorbed by a radiation shielding surrounding part of the collimator housing. The collimated beam may exit the x-ray source 105 via a dedicated port.

A filter carriage may be mounted within gantry 103 between the radiator source 105 and the subject 104. The carriage may travel in and out of the beam in the z-direction while the beam is substantially in the y-direction. The carriage may include one or more bowtie filters and/or hardening filters. During scanning, a selected collimator and/or filter 143 may be positioned in the path of the x-ray beam 106 by adjusting a position of the carriage.

In certain embodiments, the system 100 is configured to traverse different angular positions around the subject 104 for acquiring desired projection data. Accordingly, the gantry 103 and the components mounted thereon (such as the x-ray source 105 and the detector elements 102) may be configured to rotate about a center of rotation 106 for acquiring the projection data, for example, at different energy levels. Alternatively, in embodiments where a projection angle relative to the subject 104 varies as a function of time, the mounted components may be configured to move along a general curve rather than along a segment of a circle.

In one embodiment, the system 100 includes a control mechanism 108 to control movement of the components such as rotation of the gantry 103 and the operation of the x-ray source 105. In certain embodiments, the control mechanism 108 further includes an x-ray controller 110 configured to provide power and timing signals to the x-ray source 105. Additionally, the control mechanism 108 includes a gantry motor controller 112 configured to control a rotational speed and/or position of the gantry 103 based on imaging requirements.

In certain embodiments, the control mechanism 108 further includes a data acquisition system (DAS) 114 configured to sample analog data received from the detector elements 102 and convert the analog data to digital signals for subsequent processing. The data sampled and digitized by the DAS 114 is transmitted to a computing device (also referred to as processor) 116. In one example, the computing device 116 stores the data in a storage device 118. The storage device 118, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 116 provides commands and parameters to one or more of the DAS 114, the x-ray controller 110, and the gantry motor controller 112 for controlling system operations such as data acquisition and/or processing. In certain embodiments, the computing device 116 controls system operations based on operator input. The computing device 116 receives the operator input, for example, including commands and/or scanning parameters via an operator console 120 operatively coupled to the computing device 116. The operator console 120 may include a keyboard or a touchscreen to allow the operator to specify the commands and/or scanning parameters.

Although FIG. 1 illustrates only one operator console 120, more than one operator console may be coupled to the system 100, for example, for inputting or outputting system parameters, requesting examinations, and/or viewing images. Further, in certain embodiments, the system 100 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 100 either includes, or is coupled to a picture archiving and communications system (PACS) 124. In an exemplary implementation, the PACS 124 is further coupled to a remote system such as a radiology department information system, hospital information system, and/or to an internal or external network (not shown) to allow operators at different locations to supply commands and parameters and/or gain access to the image data.

The computing device 116 uses the operator-supplied and/or system-defined commands and parameters to operate a table motor controller 126, which in turn, may control a motorized table 128. Particularly, the table motor controller 126 moves the table 228 for appropriately positioning the subject 104 in the gantry 103 for acquiring projection data corresponding to the target volume of the subject 104.

As previously noted, the DAS 114 samples and digitizes the projection data acquired by the detector elements 102. Subsequently, an image reconstructor 130 uses the sampled and digitized x-ray data to perform high-speed reconstruction. Although FIG. 1 illustrates the image reconstructor 130 as a separate entity, in certain embodiments, the image reconstructor 130 may form part of the computing device 116. Alternatively, the image reconstructor 130 may be absent from the system 100 and instead the computing device 116 may perform one or more functions of the image reconstructor 130. Moreover, the image reconstructor 130 may be located locally or remotely, and the image reconstructor 130 may be operatively connected to the system 100 using a wired or wireless network. Particularly, one exemplary embodiment may use computing resources in a "cloud" network cluster for the image reconstructor 130.

In one embodiment, the image reconstructor 130 stores the images reconstructed in the storage device 118. Alternatively, the image reconstructor 130 transmits the reconstructed images to the computing device 116 for generating useful patient information for diagnosis and evaluation. In certain embodiments, the computing device 116 transmits the reconstructed images and/or the patient information to a display 132 communicatively coupled to the computing device 116 and/or the image reconstructor 130.

FIG. 2 illustrates an example x-ray source used in the imaging system of FIG. 1. In one example, x-ray source 200 may be the x-ray source 105 in FIG. 1. The x-ray source may include an x-ray tube 202 wherein an x-ray beam is generated and a collimator 204 wherein the x-ray beam is collimated to a desired beam size.

The x-ray tube 202 may include a cathode 208 and an anode 206 (also referred herein as target) positioned opposite to one another enclosed within a vacuum vessel 205. The anode 206 may be rotated about a longitudinal axis of the pillar 215 supporting the anode 206. A high voltage electrical circuit may be electrically coupled to the x-ray tube 202 and configured to supply power to the x-ray tube 202. The power supplied to the x-ray tube 202 may create a potential difference of, for example, 60 kV to 140 kV between the cathode 208 and the anode 206, thereby causing electrons generated by the cathode 208 to accelerate towards the anode 206. As the electrons collide with the anode 206 at a high velocity, at least a portion of the kinetic energy of the electrons is converted to high frequency electromagnetic radiation, or x-rays 210.

In one example, the high voltage electrical circuit may include a cathode multiplier electrically coupled to a high voltage transformer and the cathode 208, and an anode multiplier electrically coupled to the high voltage transformer and the anode 206. The cathode multiplier may be configured to supply a negative high voltage DC to the cathode 208, for example via high voltage connection, while the anode multiplier may be configured to supply a positive high voltage DC to the anode 206, for example via high voltage connection. That is, the cathode 208 and the anode 206 may carry equal voltages of different polarity. In this way, a high voltage potential difference between the cathode 208 and the anode 206 may be generated.

The x-ray tube 202 may be enclosed in a vacuum vessel 205 including a transmissive port 244. As an example, the vessel 205 may include a first radiation shield 230 arranged to block x-rays traveling in undesirable directions. The radiation shield may enclose the entire x-ray tube except for the transmissive port 244. For example, the x-ray transmissive port 244 may comprise a circular port comprising a material through which x-rays may be transmitted without absorption. The transmissive port 244 may be positioned in the vessel 205 aligned with the point of generation of x-rays on the cathode 208. The first radiation shield 230 may be made of a heavy metal such as tungsten that is able to absorb any x-ray radiation incident on the first radiation shield 230. In one example, the first radiation shield 230 surrounding the x-ray tube 202 may be of uniform thickness. In another example, the first radiation shield 230 surrounding the x-ray tube 202 may have non-uniform thickness with certain portions thicker than others such as the corners may be thickened relative to the walls. In this way, the generated x-ray is confined within the x-ray tube and may not exit the tube except via the transmissive port 244. The cylindrical first radiation shield 230 may be lined with solid thermal insulation 240.

The x-ray source may further include a collimator 204 adjoining the x-ray tube. The x-rays 210 exiting the x-ray tube 202 via the transmissive port 244 may enter the collimator. The collimator may include a first collimator blade 218 and a second collimator blade 220 positioned coaxially along a longitudinal axis A-A'. The distance between the first collimator blade 218 and the second collimator blade 220 may be adjusted to form an aperture 224. The first collimator blade 218 and the second collimator blade 220 may be moved relative to each other along the A-A' axis to adjust the aperture 224 size.

The collimator 204 may be enclosed in a second radiation shield 222 except for a port 216. A portion of the x-rays 210 may pass through the opening (aperture) between the first collimator blade 218 and the second collimator blade 220 and the transmitted x-ray beam 214 may exit the collimator via the port 216. A portion of the x-rays impinging on the first collimator blade 218 or the second collimator blade 220 may be reflected from the respective blade and the reflected x-rays 212 may be absorbed by the second radiation shield 222. In this way, the reflected rays from the collimator blades are restricted from exiting the collimator. In one example, the second radiation shield 222 surrounding the collimator 204 may be of uniform thickness. In another example, the second radiation shield 222 surrounding the collimator 204 may have non-uniform thickness with certain portions thicker than others such as the corners may be thickened relative to the walls.

The x-ray beam 214 exiting the collimator 204 may then be directed to penetrate an object (not shown), such as human anatomical parts for medical examination and diagnostic procedures. The x-rays transmitted through the object are intercepted by a detector (not shown) and an image is formed of the internal anatomy. Further, industrial x-ray tubes may be used, for example, to inspect metal parts for cracks or to inspect the contents of luggage at airports.

The first radiation shield 230 and the second radiation shield 222 may be made of tungsten instead of lead (as being commonly used for radiation shielding). Components of the first radiation shield 230 and the second radiation shield 222 may be formed by infiltrating components made of printed tungsten particles, with copper via capillary action achieved in a vacuum furnace.

The radiation shielding component may include a plurality of interconnected parts with copper infiltrated across junctions between members of adjacent parts. Each part of the plurality of interconnected parts may be a panel manufactured with tungsten by a binder jetting process. The panel may include a plurality of members and a plurality of indentations on at least two, opposite sides. Two consecutive members of the plurality of members may be separated by an indentation. The thickness of the panel is lower than 20% of a width and/or a length of the panel. The panel may be coupled to another panel by coupling a plurality of members on a side of the panel with a plurality of indentations on a side of the another panel. The copper may be infiltrated via capillary action by positioning the panel coupled to another panel in contact with copper beads or powder inside a vacuum furnace, the copper filling gaps between the plurality of members coupled to the plurality of indentations.

In one example approach, a high aspect ratio radiation shielding component may be manufactured by first individually forming panels of the final component via binder jetting or a similar process and then fusing together the panels with copper. Each panel may include complementary geometry such as members which allow mating of the panel with adjacent panels on each sides. The individual panels may be arranged together with their complementary geometries in face sharing contact and then a metal (such as copper) in the form of beads or powder may be positioned adjacent to the junctions between two adjacent panels. Adjacent panels may be fused by infiltration of metal via capillary action.

In this way, a radiation shielding component may be manufactured by fusing together panels with complementary geometries by using capillary action of metal particles. By using complementary geometry, the coupling of the individual components may be improved without use of welding or similar methods. The technical effect of using individual panels to form a larger component is that a high aspect ratio component such as a thin walled box may be manufactured using tungsten without holes, joints, and connections, thereby reducing the possibility of radiation escaping the shield.

FIG. 3 shows an example method 300 for manufacturing a radiation shielding component via a binder-jet printing process. The radiation shielding component may be used in the first radiation shield 230 and/or the second radiation shield 222 as shown in FIG. 2.

At 302, a print file including the geometry of the component to (also referred herein as part) be printed may be prepared as a computer solid model. In one example, a print file may be prepared from scratch or from a template by an operator. In another example, the print file may be retrieved from a memory of the computer. The print file may include details of the geometry such as the shape, size, and dimension of the part to be printed.

At 304, the part may be produced (printed) using a binder-jet 3D printing process. In a binder-jet 3D printing process, a binder is selectively deposited onto a powder bed, bonding the areas containing the powder together to form a solid part one layer at a time. A blade may spread a thin layer of metal (such as Tungsten) powder over a build platform. The layout of the powder on the build platform may be based on the geometry of the final component. The metal powder size may range from 0.1 to 300 micrometers in diameter. The size of the metal powder particles used may be varied based on part design and application requirements such as shielding efficiency, surface roughness, etc. In one example, for a component of a radiation shield in an x-ray tube, metal particles of average diameter of 10-50 micrometers may be used.

Then a carriage with inkjet nozzles is passed over the bed, selectively depositing a binding agent that bonds the deposited particles together. The deposition of the binding agent may also be based on the geometry of the final component. When deposition of binding agent is completed and the layer has solidified, the build platform may be moved downward and the blade re-coats the surface of the solidified metal composite layer. The binding agent is again deposited on the newly coated layer and the process is repeated until the entire component has been printed. The binding agent may include organic or inorganic binders. The binders may be thermosetting or thermoplastic polymer precursors that can be polymerized/crosslinked to form solid polymer matrix. Most binders used in binger jetting may be mixed with water/solvents or a mixture of water and solvents to enable a lower viscosity for smooth and stable jetting.

At 306, the part may be cured in an oven. Curing is a process wherein the binder solution polymerizes/crosslinks to form a polymer-metal solid composite. The curing polymerization reaction may be conducted at slightly elevated temperatures (e.g., less than 200° C.) inside the oven. As an example, the curing may be carried out in the temperature range of 65-200° C. In one example, vacuum may be applied during curing to remove any trapped air particles in the part.

At 308, the cured part may be removed from excess powder volume in the build box. At this stage, the part may be termed "green" since the parts are only bonded with the binder that has been printed to create their net shape. The remainder of the powder volume (loose) in the build box may be removed such as vacuumed away to revel the green parts, which may then be carefully removed and transferred to a furnace for infiltration. Use of such parts to manufacture an interconnected radiation shielding component by infiltrating metal between adjacent panels is elaborated in FIG. 4.

FIG. 5 shows a schematic representation 500 of a single panel 502 used in manufacturing a radiation shielding component in an x-ray device. In one example, the radiation shielding component may be used in the first radiation shield 230 and/or the second radiation shield 222 as shown in FIG. 2. In this example, panel 502 is a rectangular panel with two parallel sides including members for improved coupling with a complementary geometry of another panel. In alternate embodiments, the panel may be of other shapes such as square, polygonal, oval, round, etc. with members along one or more sides. The single panel 502 may be manufactured via the binder-jet process as elaborated in FIG. 3.

A length of the panel is designated by "L", a width of the panel is designated by "W", and a thickness of the panel is designated by "T". The panel 502 may have a high aspect ratio with the thickness of the panel being significantly smaller than the length and/or width of the panel. In one example, the thickness of the panel is less than 20% of the length and/or thickness of the panel. In another example, the thickness of the panel may be less than 3 mm while the length and/or thickness of the panel may be at least 15 mm.

A plurality of members 508 may be positioned along the lengths of the panel with indentations 510 between two successive members 508. In one example, each digit 508 may be identical with each digit being rectangular. Each indentation 510 may be formed such that a digit 508 may be completely inserted into it without any gaps between the inner walls of the indentation and the outer wall of the digit 508. Each digit may have identical length, as shown by arrow 528 and width as shown by arrow 532. The thickness of each digit, as shown by arrow 530 may be identical to the thickness T of the panel. Two consecutive members may be separated by an indentation, the length of the indentation, as shown by arrow 526 may be identical to the length 528 of a digit. Similarly, a width of the indentation and a thickness of the indentation may be identical to that of a digit such that upon coupling of adjacent panels, a digit from a panel may completely fit within a corresponding indentation of an adjacent panel. In one example, the heights of the members may be 5 mm, the width of the digit may be 3 mm, and a thickness of the digit (also the thickness of the panel) may be 3 mm.

A first side 506 of the panel may include an even number of members 508 and an odd number of indentations 510 between two successive members. A second, opposite side 504 of the panel may include an odd number of members 508 and an even number of indentations 510 between two successive members. During assembly of the panels to form a radiation shielding component, the members on the first side of a first panel may be coupled to the indentations on the second side of a second panel such that the even number of members on the first side may be interconnected with the even number of indentations on the second side. Similarly, the members on the second side of a first panel may be coupled to the indentations on the first side of a third panel such that the odd number of members on the second side may be interconnected with the odd number of indentations on the first side.

The central portion 515 of the panel 502 may include a depression 512. The depth of the depression 512 may be denoted by the arrow 534. As an example, the edges 535 of the depression 512 may be rounded. Due to the depression 512, the edge of the panel including the members may have higher thickness that the central portion 515 of the panel. A rib 514 may be positioned within the depression 512. In this example, a single rib 514 is shown to be positioned diagonally across the depression 512, the rib extending from one corner of the panel to another, opposite corner of the panel. The rib may be a curved with sides 518 of the rib being arched. In alternate embodiments, two or more ribs may be positioned on the depression 512. The rib 514 may allow improved coupling of the shielding component including the panel 502 inside a radiation shield of an x-ray system.

FIG. 4 shows an example method 400 for manufacturing a radiation shielding component using two or more individual panels with complementary geometry. The radiation shielding component may be used in the first radiation shield 230 and/or the second radiation shield 222 as shown in FIG. 2.

At 402, two or more panels with members (complementary geometries) for interlocking may be prepared. The panels may be made of tungsten and may be prepared via a binder-jet printing process (discussed in FIG. 3) or a binder reactive injection molding process where metal particles may be used to fill a mold and then infiltrated with a binder solution and cured. Alternatively, the panels may be printed layer-by-layer by binder jetting using tungsten beads. The panels may then be cured in an oven at an elevated temperature in the range of 65-200° C. Any non-bound particles may then be removed from the panel by using suction. Each panel may be panel 502 in FIG. 5. In one example, four panels with complementary interlocking members may be used to form a box-shaped radiation shielding component. In other examples, multiple interconnected panels may be used to form different geometric arrangements.

At 404, the two or more panels used for making the radiation shielding component may be arranged proximal to each other. FIG. 6A shows a first step 600 in the assembly of the multiple panels to manufacture the radiation shielding component. In this step, as described above, four individual panels 602, 604, 606, and 608 may be brought proximal to each other with the complementary geometry of each panel facing that of an adjacent panel. As an example, a first side of a panel may include even number of members 608 and odd number of indentations 610 while a second side of the panel may include odd number of members 608 and even number of indentations 610.

In one example, members on a first side of a first panel 602 may be brought proximal to the indentations on the second side of a second panel 604 such that upon coupling, the even number of members on the first side may be interconnected with the even number of indentations on the second side. Similarly, the members on the second side of a first panel 602 may be brought proximal to the indentations on the first side of a third panel 608 such that upon coupling, the odd number of members on the second side may be interconnected with the odd number of indentations on the first side of the third panel 608. The members on the second side of a third panel 608 may be brought proximal to the indentations on the first side of a fourth panel 606. The members on the second side of a fourth panel 606 may be brought proximal to the indentations on the first side of a second panel 604.

Returning to FIG. 4, at 406, the adjacent panels may be coupled such that the complementary geometries may be in face sharing contact. FIG. 6B shows a second step 620 in the assembly of the multiple panels to manufacture the radiation shielding component. In this step, as described above, four individual panels 602, 604, 806, and 608 may be coupled by interlocking the complementary geometries. As an example, members on a first side of a first panel 602 may be coupled to the indentations on the second side of a second panel 604, members on the second side of a first panel 602 may be coupled to the indentations on the first side of a third panel 608, members on the second side of a third panel 608 may be coupled to the indentations on the first side of a fourth panel 606, and the members on the second side of a fourth panel 606 may be coupled to the indentations on the first side of a second panel 604. FIG. 6C shows an embodiment 640 of the example radiation shielding component 612 formed after coupling of the complementary geometries of the four panels 602, 604, 606, and 608. Due to the inter-connected coupling, the junctions 616 between two adjacent panels do not have any significant separation (between two adjoining panels). However, at this stage, the panels are coupled together but not fused to form a single, stable structure.

Returning to FIG. 4, at 408, the assembled radiation shielding component may then be placed in a furnace at an elevated temperature. In one example, the furnace temperature may be maintained in a range between 1120° C. and 1175° C. Vacuum may be applied and air may be removed from inside the furnace. At 410, metal or alloy beads may be positioned adjacent to the assembled panels. In one example, the metal or alloy may be copper, bronze, or brass. FIG. 6D shows an example configuration 660 of metal within the assembled component 612. As an example, copper beads 614 may be filled in the area 615 enclosed by the four panels.

In alternate embodiments, inside the furnace, the metal may be delivered to a separate enclosure, outside the assembled component 612. A feed path (also referred here as stilt) may be printed on the component 612 to physically communicate between the enclosure containing copper and the component 612. The copper (in a semi molten state) may be transferred to the enclosed area 615 of the component 612 via the feed path. After completion of the manufacture of the radiation shielding component, the stilt may be removed from the component.

Returning to FIG. 4, at 412, the panels may be infiltrated (the binder may be replaced with metal), including fusing the interlocking panels to create one structural component. Gaps between complementary geometries of adjacent panels may be infiltrated with the metal or alloy particles to fuse the adjacent panels. The bead/powder delivered to an area adjacent to the panels may be in semi-molten or completely molten state due to the high temperature inside the furnace. The metal may infiltrate any gaps between the complementary geometries of two adjacent panels via capillary effect. The metal may bridge any gaps (separation) between adjacent panels, and upon solidification fuse the panels together. By carrying out the process in a vacuum furnace, possibility of oxidation of metal may be reduced.

The finished part (the radiation shielding component) may be removed from the oven. Due to the inter-connected complementary geometry and metal infiltration, the panels may be coupled effectively and fused together to form a single structure. FIG. 6E shows an example representation 680 of the finished component 624 which may be directly used in a radiation shield for x-ray as part of an x-ray generating device or an imaging device (using x-ray radiation). In this way, a complex part such as a box shaped component having a high aspect ratio (with thin walls) may be manufactured by coupling complementary geometry and then subsequently using capillary effect to infiltrate gaps between adjacent panels with metal to reinforce the coupling and fuse the panels into a single component.

In this way, a radiation shielding component may be formed by: preparing a first panel with alternating members and indentations on a first side, preparing a second panel with alternating members and indentations on a second side, interlocking the members on the first side of the first panel with the indentations on the second side of the second panel, placing interlocked first panel and second panel in contact with metal, and infiltrating a junction between the members of the first panel and the indentations of the second panel with copper to fuse the first panel with the second panel.

In one example, a system, comprises: a radiation shielding component including a plurality of interconnected parts with metal infiltrated across junctions between members of adjacent parts. In the preceding example, additionally or optionally, each part of the plurality of interconnected parts is a panel manufactured with tungsten by a binder jetting process, the binder jetting process including printing the panel layer-by-layer with tungsten beads, curing the panel, and then removing non-bound particles from the panel via suction. In any or all of the preceding examples, additionally or optionally, the panel includes a plurality of members and a plurality of indentations on at least two sides. In any or all of the preceding examples, additionally or optionally, any two consecutive members of the plurality of members are separated by an indentation. In any or all of the preceding examples, additionally or optionally, the plurality of members includes a first set of members on a first side of the panel and a second set of members on a second side of the panel, the first side opposite to the second side. In any or all of the preceding examples, additionally or optionally, the first set includes an even number of members separated by an odd number of indentations, and wherein the second set includes an odd number of members separated by an even number of indentations. In any or all of the preceding examples, additionally or optionally, a thickness of the panel is lower than 20% of a width and/or a length of the panel. In any or all of the preceding examples, additionally or optionally, the panel includes depressions and/or ribs on a surface thereof. In any or all of the preceding examples, additionally or optionally, interconnected parts include the panel coupled to another panel by coupling a plurality of members on a side of the panel with a plurality of indentations on a side of the another panel. In any or all of the preceding examples, additionally or optionally, the metal is infiltrated via capillary action by positioning the panel coupled to another panel in contact with metal beads or metal powder inside a vacuum furnace, the metal fusing the plurality of members coupled to the plurality of indentations. In any or all of the preceding examples, additionally or optionally, the metal includes one or more of copper, bronze, and brass, the metal being at a semi-molten state or a molten state in the vacuum furnace. In any or all of the preceding examples, additionally or optionally, the radiation shielding component encloses an x-ray tube or an x-ray collimator.

Another method for manufacturing comprises: forming a radiation shielding component including: preparing a first panel with alternating members and indentations on a first side, preparing a second panel with alternating members and indentations on a second side, interlocking the members on the first side of the first panel with the indentations on the second side of the second panel, placing the interlocked first panel and second panel in contact with copper, and infiltrating a junction between the members of the first panel and the indentations of the second panel with the copper to fuse the first panel with the second panel. In the preceding example, additionally or optionally, each of the first panel and the second panel are made by printing each of the first panel and the second panel layer-by-layer with tungsten beads, curing each of the first panel and the second panel, and then removing non-bound particles from each of the first panel and the second panel by suction. In any or all of the preceding examples, additionally or optionally, the members on the first side of the first panel include an even number of individual members, the individual members identical to each other, and wherein the indentations on the second side of the second panel include an even number of individual indentations, the individual indentations identical to each other. In any or all of the preceding examples, additionally or optionally, interlocking the members with the indentations includes the members on the first side of the first panel being inserted into corresponding indentations on the second side of the second panel with each digit in face sharing contact with a corresponding indentation. In any or all of the preceding examples, additionally or optionally, the infiltrating the junction includes the copper flowing through the junction via a capillary effect and fusing the members of the first panel and the indentations of the second panel, the infiltrating carried out inside a vacuum oven at a temperature higher than 200° C.

In yet another example, system for a radiation shield, comprises: three or more interconnected panels having complementary geometries coupled together with copper-filling gaps between members of adjacent panels to form an enclosed shape. In the preceding example, additionally or optionally, each panel of the three or more interconnected panels include alternating members and depressions on opposite sides therefrom, and wherein a first set of members on a first side of a first panel of the three or more interconnected panels is coupled to a first set of indentations on a second side of a second panel of the three or more interconnected panels and a second set of members on a second side of the first panel is coupled to a first set of indentations on a first side of a third panel of the three or more interconnected panels. In any or all of the preceding examples, additionally or optionally, the copper is positioned within an enclosed area formed by the interconnected panels, the inter-connected panels placed inside a heated vacuum furnace to induce the copper to fuse the members of the adjacent panels.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
    a radiation shielding component including a plurality of interconnected parts, where each part of the plurality of interconnected parts comprises a plurality of digits and a plurality of complementary indentations, with the plurality of digits of any given part of the plurality of parts inserted into, and interlocking with, the plurality of complementary indentations of each adjacent part of the plurality of parts, with metal infiltrated across junctions between outer walls of the plurality of digits in contact with inner walls of the plurality of complementary indentations.

2. The system of claim 1, wherein the radiation shielding component encloses an x-ray tube or an x-ray collimator.

3. The system of claim 1, wherein each part of the plurality of interconnected parts is a panel manufactured with tungsten by a binder jetting process, the binder jetting process including printing the panel layer-by-layer with tungsten beads, curing the panel, and then removing non-bound particles from the panel via suction.

4. The system of claim 3, wherein the panel includes the plurality of digits and the plurality of complementary indentations on at least two sides.

5. The system of claim 4, wherein any two consecutive digits of the plurality of digits are separated by an indentation of the plurality of complementary indentations.

6. The system of claim 3, wherein the plurality of digits includes a first set of digits on a first side of the panel and a second set of digits on a second side of the panel, and the plurality of complementary indentations includes a first set of complementary indentations on the first side of the panel and a second set of complementary indentations on the second side of the panel, the first side opposite to the second side.

7. The system of claim 6, wherein the first set of digits includes an even number of digits and the first set of complementary indentations includes an odd number of complementary indentations, with the even number of digits separated by the odd number of complementary indentations, and the second set of digits includes an odd number of digits and the second set of complementary indentations includes an even number of complementary indentations, with the odd number of digits separated by the even number of complementary indentations.

8. The system of claim 3, wherein a thickness of the panel is lower than 20% of a width and/or a length of the panel.

9. The system of claim 3, wherein the panel includes depressions and/or ribs on a surface thereof.

10. The system of claim 3, wherein a first side of each panel of the plurality of interconnected parts is coupled to a second side of each adjacent panel of the plurality of interconnected parts via the plurality of digits of each panel inserted into the plurality of complementary indentations of each adjacent panel.

11. The system of claim 10, wherein the metal is infiltrated across the junctions via capillary action by positioning each panel in contact with metal beads or metal powder inside a vacuum furnace, the metal fusing the plurality of digits coupled to the plurality of complementary indentations.

12. The system of claim 11, wherein the metal includes one or more of copper, bronze, and brass, the metal being at a semi-molten state or a molten state in the vacuum furnace.

13. A method for manufacturing, comprising:
    forming a radiation shielding component including: preparing a first panel with alternating digits and indentations on a first side;
    preparing a second panel with alternating digits and indentations on a second side;
    interlocking the digits on the first side of the first panel with the indentations on the second side of the second panel;
    interlocking the digits on the second side of the second panel with the indentations on the first side of the first panel;
    placing the interlocked first panel and second panel in contact with copper; and
    fusing the first panel with the second panel by:
        infiltrating a first junction between outer walls of the digits of the first panel and inner walls of the indentations of the second panel with the copper; and
        infiltrating a second junction between outer walls of the digits of the second panel and inner walls of the indentations of the first panel with the copper.

14. The method of claim 13, wherein each of the first panel and the second panel are made by printing each of the first panel and the second panel layer-by-layer with tungsten beads, curing each of the first panel and the second panel, and then removing non-bound particles from each of the first panel and the second panel by suction.

15. The method of claim 13, wherein the digits on the first side of the first panel include an even number of individual digits, the individual digits identical to each other, and wherein the indentations on the second side of the second panel include an even number of individual indentations, the individual indentations identical to each other.

16. The method of claim 13, wherein interlocking the digits on the first side of the first panel with the indentations on the second side of the second panel includes inserting the digits on the first side into corresponding indentations on the second side, with each digit on the first side in face sharing contact with each corresponding indentation on the second side; and wherein interlocking the digits on the second side of the second panel with the indentations on the first side of the first panel includes inserting the digits on the second side into corresponding indentations on the first side, with each digit on the second side in face sharing contact with each corresponding indentation on the first side.

17. The method of claim 13, wherein infiltrating the first junction includes flowing the copper through the first junction via a capillary effect and fusing the digits of the first panel and the indentations of the second panel;

wherein infiltrating the second junction includes flowing the copper through the second junction via the capillary effect and fusing the digits of the second panel and the indentations of the first panel; and wherein the infiltrating of the first junction and the second junction is carried out inside a vacuum oven at a temperature higher than 1120° C.

18. A system for a radiation shield, comprising:

three or more interconnected panels having complementary geometries including a plurality of digits separated by a plurality of indentations, with the plurality of digits of any given panel of the three or more interconnected panels coupled together with the plurality of indentations of each adjacent panel of the three or more interconnected panels via copper-filled junctions between the plurality of digits of the any given panel and the plurality of indentations of each adjacent panel to form an enclosed shape.

19. The system of claim 18, wherein each panel of the three or more interconnected panels includes the plurality of digits and the plurality of indentations on opposite sides therefrom, and wherein a first set of digits of the plurality of digits on a first side of a first panel of the three or more interconnected panels is coupled to a first set of indentations of the plurality of indentations on a second side of a second panel of the three or more interconnected panels, and a second set of digits of the plurality of digits on a second side of the first panel is coupled to a second set of indentations of the plurality of indentations on a third side of a third panel of the three or more interconnected panels.

20. The system of claim 18, wherein the copper is positioned within an enclosed area formed by the three or more interconnected panels, the three or more interconnected panels placed inside a heated vacuum furnace to induce the copper to fuse the plurality of digits of the any given panel to the plurality of indentations of each adjacent panel.

* * * * *